United States Patent [19]

Cohen

[11] Patent Number: 4,611,600

[45] Date of Patent: Sep. 16, 1986

[54] OPTICAL FIBER PRESSURE TRANSDUCER

[75] Inventor: Donald M. Cohen, Miami, Fla.

[73] Assignee: Cordis Corporation, Miami, Fla.

[21] Appl. No.: 553,581

[22] Filed: Nov. 21, 1983

[51] Int. Cl.$^4$ ............................................... A61B 5/02
[52] U.S. Cl. .................................... 128/667; 128/675; 128/748; 73/705
[58] Field of Search ................. 73/705; 128/748, 667, 128/673, 675, 634; 250/231 P

[56] References Cited

U.S. PATENT DOCUMENTS

| 3,123,066 | 3/1964  | Brumley       | 128/634   |
| 3,159,750 | 12/1964 | Kazan         | 73/705 X  |
| 3,249,105 | 5/1966  | Polanyi       | 73/705 X  |
| 3,273,447 | 9/1966  | Frank         | 73/705 X  |
| 3,686,958 | 8/1972  | Porter et al. | 128/748 X |

OTHER PUBLICATIONS

Matsumoto et al, J. Med. Eng. and Tech., vol. 2, No. 5, Sep. 1978, pp. 239–242.

Primary Examiner—Kyle L. Howell
Assistant Examiner—John C. Hanley
Attorney, Agent, or Firm—Yount & Tarolli

[57] ABSTRACT

The optical blood pressure catheter includes an elongated flexible light conductor for transmitting light received at its proximal end to its distal end and for transmitting light received at the distal end back to the proximal end. A pressure transducer is located adjacent the distal end and includes a light reflector which is spaced along a light path from the distal end and is fixed in position relative thereto so as to receive and reflect light emitted from the distal end back into the distal end. A pressure responsive membrane is located intermediate the distal end and the reflector and is movable transversely of the light path in dependence upon the pressure exerted on the exterior surface of the membrane. A shutter carried by the membrane moves therewith transversely of the light path for blocking light along the light path so that the light received by the distal end is attenuated in dependence upon the pressure exerted on the membrane.

2 Claims, 7 Drawing Figures

OPTICAL FIBER PRESSURE TRANSDUCER

BACKGROUND OF THE INVENTION

This invention relates to the art of measuring intravascular blood pressure and, more particularly, to apparatus for directly measuring the blood pressure at the location of interest by means of a catheter having a transducer tip insertable into the blood stream.

Catheters have been used in the art for monitoring variations in pressure within the blood stream at various locations throughout the cardiovascular system. It has been accepted practice to insert the distal end of a catheter into a blood vessel and then connect the proximal end of the catheter outside the body, to an external transducer at which pressure variations are measured. Such external transducers are considered relatively inexpensive and employ disposable fluid filled catheters. However, in use such catheters require periodic flushing to avoid thrombus formation. Also, the frequency response characteristics are often compromised by the mechanical properties of the catheter, inclusion of small air bubbles and by body motion artifact. The blood pressure must be transmitted from the interior of the blood vessel through the catheter tubing by means of the fluid column therein before it can act on the external transducer. Consequently, the frequency response for such an external transducer is also compromised by the relatively large mass of the fluid column within the catheter tubing.

Other approaches to measuring intravascular blood pressure have included employing catheter tip transducers insertable into the blood stream. Such catheter tip transducers provide direct pressure monitoring in that they transduce blood pressure at the region of interest rather than attempting to couple the dynamic waveform hydraulically, as in the external transducers. Many of the catheter tip transducers employ semiconductors and other sensing elements of the resistive and/or capacitive variety at the catheter tip. An electrical signal is generated or modulated at the transducer and transmitted through the length of the catheter to meters and the like located externally of the body being tested. Such semiconductor tip transducers are expensive and, hence, the high cost is not compatible with their being disposable units. Instead, there is a tendency to reuse the product and, despite sterilizing or autoclaving there remains a potential to transfer proteins, which may be antigenic, from one patient to a successive one. Another potentially troublesome feature of such semiconductor transducer tips is the use of electricity to power the sensor. The use of electricity not only renders the device susceptible to electromagnetic interference, but also introduces the possible hazard of arrhythmia induction.

To overcome some of the noted difficulties, other attempts in determining blood pressure in a cardiovascular system have included catheters employing optically based pressure transducer tips at the distal end. Such devices typically take the form as illustrated in U.S. patents to Polyanyi, U.S. Pat. No. 3,249,105 and Franke U.S. Pat. No. 3,215,135. Each of these devices employs a catheter having fiber optic means extending the length of the catheter to the distal end thereof at which the fiber optic means is in optical communication with a pressure transducer. The pressure transducers in Polyanyi and Franke, supra, take the form of a diaphragm covering the end hole of the catheter. The diaphragm is located in front or distal to the end of the fiber optical means and then receives light and reflects it back into the fiber optic means for transmission to an externally located meter. Since the transducer tip is inserted into the blood stream of a patient, the blood pressure deflects the diaphragm causing modulation of the light intensity so that the meter provides an indication of blood pressure.

Such catheters employing diaphragm covered end holes actually measure total pressure rather than the desired measurand; namely, static pressure. Thus, by aligning the end hole of a catheter with the direction of blood flow, kinetic energy terms are introduced. If the catheter end hole is directed upstream, the kinetic term will be added to the pressure, and, if the end hole is facing downstream, the kinetic term will be subtracted from the pressure. The magnitude of the error will vary with flow rate. This error will vary during the course of a cardiac cycle and will distort the shape and magnitude of a pressure wave. In the pulmonary artery, the kinetic pressure may be on the order of 10% of total pressure at rest and 50% of total pressure at a cardiac output equal to three times that at rest. The importance of the kinetic pressure error is particularly great in stenotic areas where velocities are high.

The noted problems with catheters employing diaphragm covered end holes to monitor pressure may be alleviated with a tip transducer that employes side port monitoring of pressure rather than end hole monitoring of pressure. The kinetic contribution is minimal when measuring pressure perpendicular to the blood flow. One such device is known and is reported in a 1978 article entitled "The Development of Fibre Optic Catheter Tip Pressure Transducer", Journal of Medical Engineering and Technology, Vol. 2, No. 5, by H. Matsumoto and M. Saegusa. As disclosed in that article, the Matsumoto optical sensor employs a tipped transducer having side port monitoring of pressure. The pressure transducer measures pressure acting at right angles to blood flow. A membrane is responsive to the pressure and causes movement of a mirror, which is mounted in cantilevered fashion to the membrane, within the cavity of the transducer tip. The mirror serves to reflect light received from fiber optic means extending the length of the catheter so that the intensity of light returned by way of the fiber optic means to a measuring device located outside the body is modulated in accordance with the static pressure. However, this structure requires precise alignment between the distal end of the fiber optic and the cantilevered mounted mirror so that the deflected light as measured by the externally located meter will be properly indicative of the static pressure. Additionally, there is a nonlinearity in the response characteristics of such a device both because the cantilevered mounted mirror undergoes an angular displacement and nonlinear displacement.

SUMMARY OF THE INVENTION

It is an object of the present invention to provide a catheter having an optical fiber pressure transducer tip contructed in a manner so that it is sufficiently inexpensive to be disposable.

It is still a further object of the present invention to provide an improved construction wherein the optical tip transducer employs a side port for measuring static pressure as opposed to an end hole which is subject to kinetic pressure errors.

It is a still further object of the present invention to provide an improved construction wherein a membrane covered side port is responsive to pressure to displace a shutter transversely between the distal end of a fiber optic means and a fixed mirror for purposes of modulating the intensity of light reflected back into the fiber optic means in direct proportion to the static pressure.

In accordance with the present invention, the optical blood pressure catheter includes an elongated flexible light conducting means for transmitting light received at a first end to a second end thereof and for transmitting light received at said second end back to the first end. A pressure sensitive transducer is secured adjacent the second end and includes a light reflector which is spaced along an optical path from the second end and is fixed in position relative thereto for receiving and reflecting light from and back into said second end. A pressure sensitive membrane is located alongside of the optical path and is responsive to pressure acting thereon so as to deflect transversely to the light path in response to the pressure. A shutter is mounted to the membrane for movement therewith to attenuate the amount of light reflected back into the second end in dependence upon the pressure exerted on the membrane.

BRIEF DESCRIPTION OF THE DRAWINGS

The foregoing and other objects and advantages of the present invention will become more apparent from consideration of the following description as taken in conjunction with the accompanying drawings, wherein.

DETAILED DESCRIPTION OF PREFERRED EMBODIMENT

Figure 1:
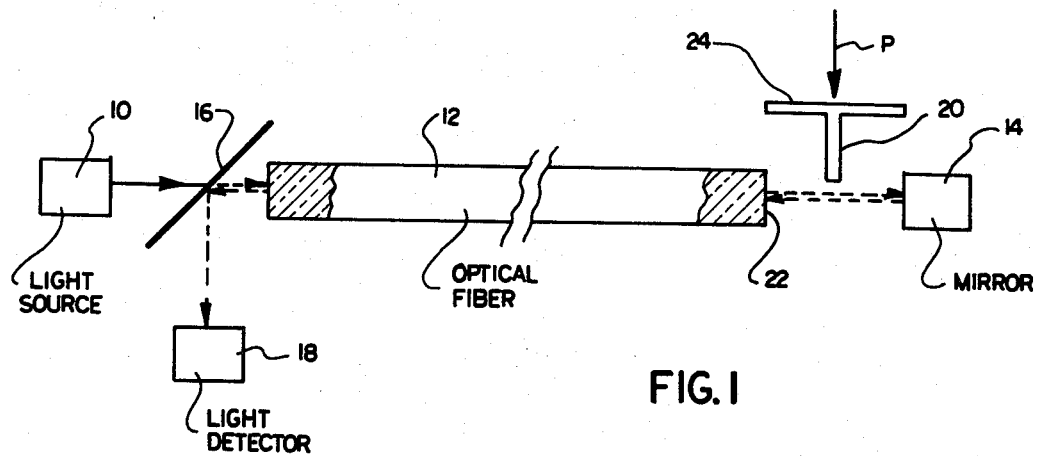
FIG. 1 is a schematic illustration of the invention.

Reference is now made to the schematic diagram of FIG. 1 which provides a simplified version of the present invention and which basically includes a light source 10 for emitting light along an optical axis defined by an optical fiber 12 along a path so that the light strikes and is then reflected back from a mirror 14. The reflected light is transmitted by way of the same optical fiber 12 and is diverted, as by a beam splitter 16, to a light detector 18. The light detector 18 serves to measure the amount of the light reflected by mirror 14. The amount of light reflected back into the optical fiber is varied in dependence upon the position of a shutter 20 located intermediate the distal end 22 of the fiber and the mirror 14. Shutter 20 is mounted to or fabricated as a contiguous part of a polymeric membrane 24 which deflects in response to blood pressure acting on the membrane in a direction, as indicated by the arrow P, which is transverse to the axis of fiber 12. As the blood pressure increases, the shutter interrupts more and more light and this is measured by the light detector 18.

It is to be particularly noted that only shutter 20 moves transversely of the optical axis as the distal end of the optical fiber 12 and the mirror 14 are in fixed relationship to each other along the optical axis. Consequently, unlike prior art catheter transducer tips, there is no need to account for motion of the mirror with respect to the fiber, which motion causes nonlinear behavior (transduction). Since the relationship between the mirror and the optical fiber is fixed, there is no need for precise alignment of the mirror with the fiber. Thus, the output is not greatly affected if the mirror is skewed off axis laterally, vertically and/or longitudinally, since the relationship remains fixed. This design, therefore, is very tolerant of assembly techniques. Moreover, the shutter is optically black to absorb the incident light. Consequently, any angular displacement of the shutter has only a minor affect on the system.

Figure 2:
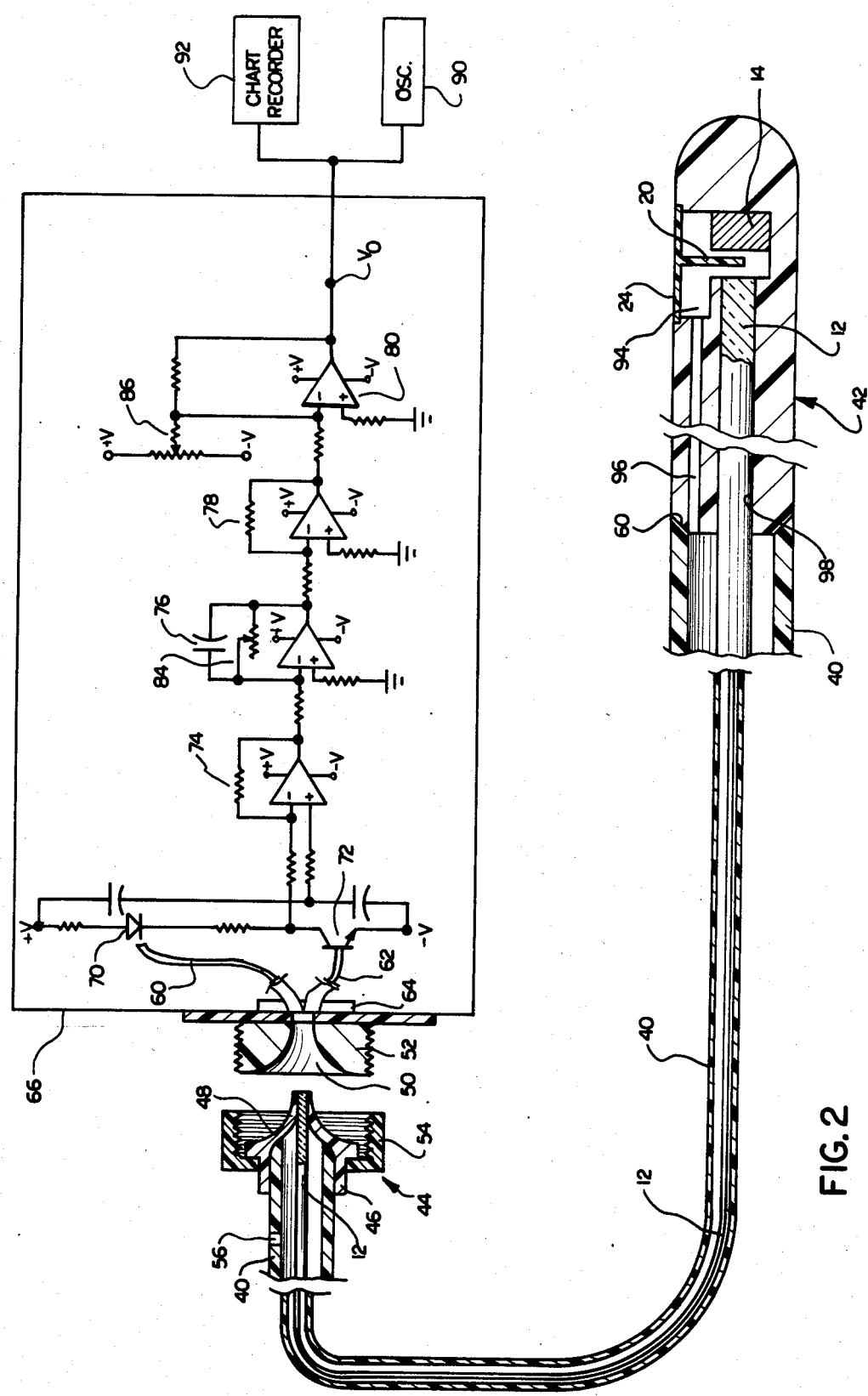
FIG. 2 is a diagrammatic representation of the invention, partly in section, and with the proximal and distal ends enlarged.

Having now briefly described the invention relative to the simplified schematic of FIG. 1, reference is now made to FIG. 2 which illustrates a preferred embodiment of the invention. To facilitate the description, like components in FIGS. 1 and 2 are identified herein with like numerical references. The single optical fiber 12 preferably takes the form of a step index fiber such as one known as the Du Pont Pifax P-140 (attenuation less than 700 dB/km at 640 nm). The core diameter equals 368 micrometers, and clad diameter equals 400 micrometers nominally. The numerical aperture is 0.53. This optical fiber 12 is housed within a thin wall catheter 40 such as that provided by Cordis Corporation and known as the Cordis Fr5 thin wall catheter. This catheter has a diameter on the order of 0.066 inches and is constructed of a plastic material such as polyurethane. At the distal end, catheter 40 is fitted with a transducer tip assembly 42 which carries the membrane 24, the shutter 20 as well as the mirror 14. At the proximal end, the catheter is fitted with a connector 44 for connecting the optical fiber 12 to a beam splitter or optical fiber bifurcation. The two light paths are connected to a light source and a light detector. The connector 44 may be constructed by modifying conventional fiber optic connector parts provided by AMP, Inc. and, for example, the connector parts include plastic ferrule 46 which is secured to the proximal end of the catheter. The tip of the ferrule 46 has a portion 48 which serves to guide an extended portion of the optical fiber into the corresponding shaped aperture 50 of a female connector 52. The male connector 52 is threaded and cooperates with an internally threaded female connector 54 located on the proximal end of the catheter. These secure the catheter in place in a reusable fashion. The male connector 52 provides communication for the proximal end of the optical fiber 12 with a bifurcated fiber optic structure having a light transmission portion 60 and a light receiving portion 62 which are joined together with a mounting plate 64 secured at one side of a shielded electronic housing 66. The bifurcated end is exposed to the aperture 50 for communication with the proximal end of the optical fiber 12. The optical fiber portions 60 and 62 may be constructed of the same material as that employed for optical fiber 12. During operation, light emitted from a light source in the form of an ultrabright light emitting diode (LED) 70 is transmitted through the transmitting optical fiber 60 and, thence, through the length of optical fiber 12. Light emerging from the distal end of the optical fiber 12 is either attenuated by shutter 20 or is reflected back by mirror 14 and is then transmitted from distal end to proximal by the optical fiber 12 and the receiving fiber 62 where it is detected by a silicon PIN photodiode 72.

The circuitry illustrated in FIG. 2 is shown as being housed within shielded housing 66. In addition to the light emitting diode 70 and the photodiode 72, the circuitry includes a four stage amplifier including amplifier stages 74, 76, 78 and 80. The components are chosen such that during operation, a constant current flows through the light emitting diode 70. This is on the order of 30 milliamperes with a power dissipation of approximately 60 milliwatts. The luminous efficacy is on the order of 147 lumens per watt. The sensitivity of the photodiode 72 is approximately one ampere per watt. The detector circuitry provides an output voltage $V_0$ having a magnitude which varies in dependence upon the current flowing through the photodiode 72 and which, in turn, varies with the amount of light it receives from the receiving optical fiber 62. This signal is buffered and amplified by the first amplifier stage 74.

This is amplified and low pass filtered by the amplifier stages 74 and 76. Amplifier stage 76 has a gain adjustment in its feedback path taking the form of a potentiometer 84 so that the operator may adjust the gain and, hence, the magnitude of the output voltage $V_0$. The output from the amplifier stage 76 is again amplified by stages 78 and 80. Amplifier stage 80 has an offset voltage applied to its inverting input through a potentiometer 86. This DC bias voltage is adjustable by the wiper arm of the potentiometer. This adjustment serves to null out the ambient conditions of light reflected from fiber 60 back into the receiving optical fiber 62 as well as that due to the initial positioning of the shutter 20 relative to the distal end of the optical fiber 12. This presents a zeroing or reference level against which measurements may be made. The output voltage $V_0$ will vary with light received at the photodiode 72 as a result of variations of movement of the shutter 20 in response to variations in blood pressure exerted against the membrane 24. These variations may be observed as with an oscilloscope 90 and a permanent record may be had as with the use of a chart recorder 92.

To facilitate an understanding the preferred embodiment of the invention, both the proximal and the distal end of the catheter are shown as being enlarged in FIG. 2. The transducer tip assembly 42 is formed of the same material as that of the catheter 40 and this is a plastic material, such as a polyurethane. During the molding process, a cavity 94 is provided and serves as the pressuring measuring chamber and this cavity opens so as to provide a side port to which the membrane 24 is secured. Mirror 14 is mounted in the cavity as shown in FIG. 2, with its light reflecting surface facing the distal end of the optical fiber 12. Mirror 14 may be constructed of polished metal or metal coated plastic. In addition to cavity 94, the molding process provides longitudinal passages 96 and 98 which extend from cavity 94 so as to communicate with the interior of the catheter 40. Passage 96 serves as an atmospheric vent so that atmospheric pressure is communicated to the cavity 94 by way of the interior of the catheter 40 which leads to an aperture 56 located adjacent the proximal end thereof. The second passage 98 receives the distal end of the optical fiber 12 as it extends beyond the catheter 40. The distal end of the catheter makes lapping engagement with one end 60 of the transducer tip assembly and the materials are bonded together, as with an adhesive, solvent bonding or other suitable bonding process.

As is apparent, the membrane 24 and shutter 20 are formed as a unitary structure and is preferably constructed from a material which exhibits some level of resiliency and which is preferably optically opaque. One material for this is a black pigmented silastic. The shutter has a thickness, as viewed in FIG. 2, on the order of 0.003 inches and this is sufficient to cause a one decade decrease in output from the fully open to the fully closed position. The membrane 24 deflects transversely of the optical axis on the order of 0.001 inches for every 100 mm Hg applied. The deflection of the center of the membrane is linearly related to the pressure applied to it.

Figure 3:
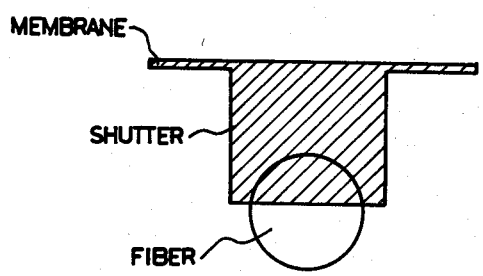
FIG. 3 is a schematic illustration of a membrane-shutter arrangement.
Figure 4:
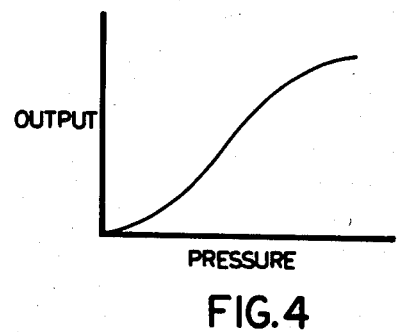
FIG. 4 is a graphical representation of measured output voltage as a function of pressure for the arrangement in FIG. 2.
Figure 5:
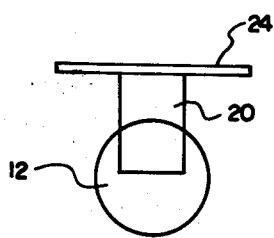
FIG. 5 is a schematic illustration of a membrane-shutter arrangement.

Preferably, the width of the shutter should be less than the diameter of optical fiber 12 at its distal end in order to obtain a linear output of the voltage $V_0$ with respect to applied pressure. In FIG. 3, there is illustrated a membrane-shutter arrangement wherein the shutter is wider than the diameter of the distal end of the optical fiber. With such a construction, it has been determined that the output, as viewed in FIG. 4, will vary in a nonlinear manner with respect to applied pressure. Preferably, the shutter takes the form as illustrated in FIG. 5 wherein shutter 20 is illustrated as having a width which is less than the diameter of the distal end of the optical fiber 12.

Figures 6, 7:
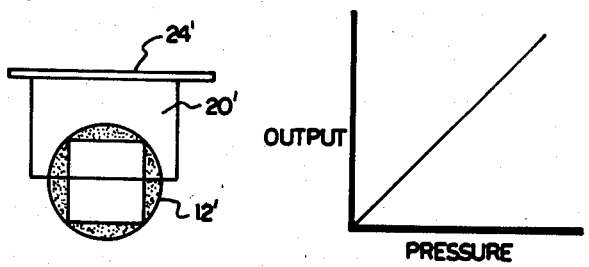
FIG. 6 is a schematic illustration of another membrane-shutter arrangement.
FIG. 7 is a graphical representation of measured output voltage as a function of pressure for the arrangements in FIGS. 5 and 6.

An alternative embodiment is illustrated in FIG. 6, wherein the shutter 20' has a width greater than the diameter of the optical fiber 12'. However, the distal end of the optical fiber 12' in this embodiment is masked so as to provide a rectangular aperture through which light passes. With the construction shown in either FIGS. 5 or 6, the output will vary in a linear manner with respect to pressure as is illustrated in FIG. 7. In the embodiment of FIG. 5, where the shutter width is less than the diameter of the fiber, the output voltage $V_0$ can be considered as being proportional to the overlapping area of the shutter with respect to the fiber. Changes in pressure will cause linear changes in the overlapping areas. With respect to the embodiment of FIG. 6 wherein the optical fiber has a rectangular aperture through which light may be emitted or receives, the shutter 20' may be of a width equal to or greater than that of the aperture. It is seen that movement of the shutter transversely of the optical axis of the optical fiber will result in an output which varies linearly with the pressure.

In operation, the catheter 40 with its transducer tip 42 attached thereto is inserted into a blood vessel of a cardiovascular system until the transducer tip reaches the site of interest. Cavity 94 is vented to the atmosphere by way of the vent 96 and the passageway through the catheter to the opening 56. Consequently, pressure exerted on the exterior of membrane 24 in excess of atmospheric pressure will cause deflection of the membrane inwardly of the cavity to cause similar movement of the shutter 20 to attenuate the light flux incident thereon. Conversely, pressure less than atmosphere will result in an outward deflection of the membrane 24 and thus also the shutter 20. The light incident on the mirror is largely reflected back into the fiber for detection at the proximal end. With the coupling at the proximal end secured in place and with the power turned on, light emitted from the diode 70 will be transmitted by way of optical fibers 60 and 12 to the cavity 94. With the gain properly adjusted, as with potentionmeter 84, the operator may observe the output voltage $V_0$. Before the catheter is inserted into the cardiovascular system, the operator may note some output voltage which is indicative of back reflection from optical fiber 60 to optical fiber 62, as well as back reflection within the cavity. These may be zeroed out by adjusting potentiometer 86 to apply an offsetting DC bias so that $V_0$ equals zero when the applied pressure is equal to atmospheric pressure. With these adjustments made, the catheter may be inserted in the cardiovascular system to the site of interest so that variations in pressure with respect to time may be measured and observed exterior of the body as with the oscilloscope 90 and permanent records may be made as with the use of chart recorder 92.

It has been found that the frequency response of the transducer tip catheter disclosed herein is fairly flat over a range such that the 3 db power point is at a frequency serveral times higher than the peak frequency content of the physiologic pressure signal. It has also been found that pressure may be measured over a range extending from −100 mm Hg to +300 mm Hg. Moreover, the catheter tip transducer as disclosed in FIG. 2 has a relatively low cost of manufacture and, hence, is disposable and need not be reused as in the case of expensive transducers employing semiconductor pressure measuring devices.

Whereas the invention has been described in conjunction with a preferred embodiment, it is to be appreciated that various modifications and arrangements may be made without departing from the spirit and scope of the invention as defined by the appended claims.

What is claimed is:

1. Apparatus for measuring blood pressure at a remote location, comprising:
   an elongated flexible tubular member;
   a blood pressure transducer assembly including a transducer housing secured to the distal end of said member and being adapted to be positioned at a said remote location;
   light conducting means carried within said tubular member for transmitting light to and receiving light from said transducer assembly;
   said transducer housing having a cavity in light communication with said light conducting means, light reflecting means mounted in said cavity and fixed in position relative to said light conducting means for receiving light therefrom and reflecting light back thereto, shutter means located in said cavity intermediate said light conducting means and said light reflecting means and movable transversely thereof for varying the amount of light reflected back into said light conducting means, said cavity having a side opening, a pressure sensitive membrane covering said opening and being responsive to exterior pressure applied thereto to move inwardly or outwardly of said cavity, said shutter means being carried by said membrane for blocking light in dependence upon said pressure, said light conducting means is a single optical fiber of circular cross section, and said shutter means is rectangular and aligned with the distal end of said optical fiber and is of a uniform width transversely of the distal end less than the diameter of the optical fiber by an amount sufficient to linearly attenuate light as a function of pressure.

2. Apparatus for measuring blood pressure at a remote location, comprising:
   an elongated flexible tubular member;
   a blood pressure transducer assembly including a transducer housing secured to the distal end of said member and being adapted to be positioned at a said remote location;
   light conducting means carried within said tubular member for transmitting light to and receiving light from said transducer assembly;
   said transducer housing having a cavity in light communication with said light conducting means, light reflecting means mounted in said cavity and fixed in position relative to said light conducting means for receiving light therefrom and reflecting light back thereto, shutter means located in said cavity intermediate said light conducting means and said light reflecting means and movable transversely thereof for varying the amount of light reflected back into said light conducting means, said cavity having a side opening, a pressure sensitive membrane covering said opening and being responsive to exterior pressure applied thereto to move inwardly or outwardly of said cavity, said shutter means being carried by said membrane for blocking light in dependence upon said pressure, said light conducting means is a single optical fiber of circular cross section, and the distal end of said optical fiber is masked so as to provide a rectangular-shaped light emitting-receiving aperture of a width uniformly less than that of said shutter means by an amount sufficient to obtain linear attenuation of light with membrane movement as a function of pressure.

* * * * *